(12) United States Patent
Vaughn

(10) Patent No.: US 10,098,833 B1
(45) Date of Patent: Oct. 16, 2018

(54) FORMULATION AND METHOD OF USE

(71) Applicant: Amelia Vaughn, Tupelo, MS (US)

(72) Inventor: Amelia Vaughn, Tupelo, MS (US)

(*) Notice: Subject to any disclaimer, the term of this patent is extended or adjusted under 35 U.S.C. 154(b) by 20 days.

(21) Appl. No.: 14/930,786

(22) Filed: Nov. 3, 2015

Related U.S. Application Data

(60) Provisional application No. 62/123,660, filed on Nov. 24, 2014.

(51) Int. Cl.
| | |
|---|---|
| *A61K 8/02* | (2006.01) |
| *A61K 8/73* | (2006.01) |
| *A61Q 19/00* | (2006.01) |
| *A61K 8/97* | (2017.01) |
| *A61K 36/899* | (2006.01) |
| *A61K 36/8998* | (2006.01) |
| *A61Q 15/00* | (2006.01) |
| *A61K 45/06* | (2006.01) |

(52) U.S. Cl.
CPC ............. *A61K 8/97* (2013.01); *A61K 36/899* (2013.01); *A61K 36/8998* (2013.01); *A61K 45/06* (2013.01); *A61Q 15/00* (2013.01); *A61Q 19/00* (2013.01); *A61Q 19/007* (2013.01); *A61K 2800/5922* (2013.01); *A61K 2800/805* (2013.01)

(58) Field of Classification Search
None
See application file for complete search history.

(56) References Cited

U.S. PATENT DOCUMENTS

| | | | | |
|---|---|---|---|---|
| 2006/0204755 | A1* | 9/2006 | Torii | A61L 15/60 428/402 |
| 2010/0233110 | A1* | 9/2010 | Cohen | A61K 8/022 424/60 |

FOREIGN PATENT DOCUMENTS

JP      62-003752 A   *   1/1987

OTHER PUBLICATIONS

English Translation of JP 62-003752 A, retrieved from https://www4.j-platpat.inpit.go.jp/eng/tokujitsu/tkbs_en/TKBS_EN_GM101_Top.action on Oct. 20, 2017 (Year: 2017).*

* cited by examiner

*Primary Examiner* — Robert T. Crow
*Assistant Examiner* — John P Nguyen
(74) *Attorney, Agent, or Firm* — Veritay Group IP; Susan Fentress

(57) ABSTRACT

The present subject matter includes a product formulation made by the process including the steps of: adding a sufficient amount of water to cover a group of long grain seeds to form a first mixture; adding a sufficient amount of water to cover a group of whole grain seeds to form a second mixture; boiling the first and second mixtures, cooling the first mixture to form a thin colorless liquid; separating any solid seeds from the thin colorless liquid; cooling the second mixture to form an opaque thick liquid; separating any solid seeds from the opaque thick liquid; combining the thin colorless liquid and the opaque thick liquid to form a third mixture; cooling the third mixture to allow the formulation of a film; heating the film to form a porous material; cooling the porous material to form a powder residue; and processing the powder residue to form a formulation. The formulation can be used in various cosmetics, and to treat subject in need of treatment for skin conditions, such as acne.

9 Claims, No Drawings

FORMULATION AND METHOD OF USE

CROSS-REFERENCE TO RELATED APPLICATIONS

This application claims the benefit of U.S. provisional patent application Ser. No. 62/123,660 filed Nov. 24, 2014 under 35 U.S.C. § 119(e), hereby specifically incorporated by reference.

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not Applicable.

STATEMENT REGARDING PRIOR DISCLOSURES BY THE INVENTOR OR A JOINT INVENTOR

Not Applicable.

BACKGROUND OF THE INVENTION

Field of the Invention

This disclosure relates to a formulation and method to use the formulation for skin care treatment, various cosmetics (such as eye shadow), personal care, such as, deodorant and sport powder, which is used for controlling wetness.

Description of Related Art including information disclosed under 37 CFR 1.97 and 1.98. Talcum powder is a soft, white powder developed from talc, or magnesium silicate, a mineral composed primarily of magnesium, silicon and oxygen. When it is finely ground, talc absorbs moisture and helps reduce friction. Talcum powder poisoning may occur when someone accidentally or intentionally breathes in or swallows talcum powder. Additionally, it has been suggested that talcum powder might cause cancer in the ovaries if the powder particles (applied to the genital area or on sanitary napkins, diaphragms, or condoms) were to travel through the vagina, uterus, and fallopian tubes to the ovary, In view of the potential risk of using powder with talc it is desirable to find alternative formulations.

BRIEF SUMMARY OF THE INVENTION

The present subject matter includes a product formulation made by the process including the steps of: adding a sufficient amount of water to cover a group of long grain seeds to form a first mixture; adding a sufficient amount of water to cover a group of whole grain seeds to form a second mixture; boiling the first and second mixtures; cooling the first mixture to form a thin colorless liquid; separating any solid seeds from the thin colorless liquid; cooling the second mixture to form an opaque thick liquid; separating any solid seeds from the opaque thick liquid; combining the thin colorless liquid and the opaque thick liquid to form a third mixture; cooling the third mixture to allow the formation of a film; heating the film to form a porous material; cooling the porous material to form a powder residue; and processing the powder residue to form a formulation. The formulation can be used in various cosmetics, and to treat subject in need of treatment for skin conditions, such as acne.

the subject matter presented includes an Avgen formulation made by the process. The process includes the step of: adding a sufficient amount of water to cover plant embryos, where two or more long grain seeds is mixed together to form a "caryica". Boiling the mixture; thick layer of liquid is formed using two or more outer-shells of a whole grain seed that dissolve to from a mixture called a "cucurmosus", separating the liquid phase; cooling the mixture to form a saptrix film. A saptrix is a transparent liquid film on top and sludgy liquid on the bottom. After at least 12 to 24 hours have elapsed from of the separating step, then the mixture is heated to remove the water. Cooling the mixture to form a saptrix for at least 6 to 12 hours. Heating the mixture to form a liquid to solid phase; saptrix is place in the oven at 350° F. for at least 15 to 20 minutes. Saptrix will form into a crape having a thin sheet of solid glaze with shiny coating specks; processing the crape to form an Avgen formulation. The Avgen formulation can also provide relief to wetness due to antiperspirant and dryness due to sweating hands. Additionally, the Avgen formation can be used in various cosmetics and to treat a subject in need of treatment for skin disorders.

DETAILED DESCRIPTION OF THE INVENTION

The present invention may be understood more readily by reference to the following detailed description of the invention. It is to be understood that this invention is not limited to the specific devices, methods, conditions or parameters described herein, and that the terminology used herein is for the purpose of describing particular embodiments by way of example only and is not intended to be limiting of the claimed invention. Also, as used in the specification containing the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value.

Plants include several parts: the bran, endosperm and embryo. The embryo, during germination forms the roots and buds of the plant. It contains protein, minerals, Vitamin B Complex, Vitamin E, unsaturated fatty acids, fiber, folic acid and enzymes. Preferably, the embryo is derived from long grain rice is usually described as rice that is about four or five times as long as it is wide. Typical length measurements for a single grain vary between about 0.27 to 0.35 inch (7 to 9 millimeters). Most of the long grain types grown today were developed from the rice type *Oryza sativa* var. *indicia*, which produced the famous Indian basmati rice. Alternately, the plant embryo is derived from a barley plant.

The present formulation is made by a process involving the steps: of adding a sufficient amount of water is used to cover long grain seeds, such as rice to form a first mixture. A caryica is two or more long grain seeds mixed together during separating from ingredients. Simultaneously, adding a sufficient amount of water to cover a group of whole grain seeds to form a second mixture. The whole grain seeds include: wheat, oats and barley, or others. A cucurmosus means two or more outer-shell of a whole grain seed dissolved to form a thin layer of a liquid. The first and second mixture with the seeds is brought to a boil while stirring. A mixture is a substance made by mixing other substances together. The mixture is boiled for 1 to 1 ½ hours. The mixtures are cooled to room temperature. The first mixture forms a thin colorless liquid. Any remaining solid seeds are separated from the thin colorless liquid and saved to be used in a formulation to provide relief from skin wetness. The second mixture forms an opaque thick liquid. Any remaining solid seeds are separated from the thick opaque liquid and are saved to be used in a formulation to provide relief from wetness. The thin colorless liquid and the opaque thick liquid are combined to form a third mixture. The third mixture is cooled to allow the formation of a film. A saptrix is a transparent liquid film on top and sludgy liquid on the bottom. The film is heated to form a porous material. After 12-24 hours, the liquid is heated in an open pot at between 350-450 degrees F. for about 1 hour to remove the water and leave a porous material that can be referred to as "crapes". Crapes is a sheet of a solid glaze with shiny coating specks. The porous material is cooled to form a powder residue; and can be further processed to form a formulation. The term "Avgen" means a liquid formed into a solid using two or more long-grain and whole grain seed mixtures together to form a formulation.

The powder can be crushed or mixed in a mixer to form a powder formulation. A powder is made of fine dry particles produced by the grinding, crushing, or disintegration of a solid substance. With respect to the skin care application, the powder formulation can be blended with extract of aloe vera wheat extract, citric acid, flavoring and natural soy.

According to the present invention, it is also effective for antiperspirant, most particularly keeping dry from perspiration, although, the formulation and Talc have characteristic in many products, but different result in the formula. The remaining solid seeds separated from the liquids, by the previously described process, are dried and crushed to form a dry seed powder and the dry seed powder is mixed with the powder residue, obtained in the previously described process, to form an anti-wetness formulation.

The formulation can be used for sports applications, where the skin needs to be dry and also as a deodorant.

TABLE 1

| Date | Subject | Sport Category | |
|---|---|---|---|
| 2011 | A | Professional Basketball | Yeah, that's cool, that's cool I mean the powder always tightened up the grip. Wished it had gotten it tighter earlier because it's tight now. The Product, you can't explain it, once you get it and you get the ball - and you don't want to pass it. |
| 2011 | B | Professional Basketball | Used the Product in the game, it's was great, it is a great powder to use to grip the basketball and control the basketball well, you know, it was great. Yeah, it dried my hands every time I used it when they were sweaty' I put it on and it dried my hands. Yeah, I caught the ball afterwards; the ball was slippery and I put the Product on it and I could grip the ball and it would be more effective. I probably used it twice- before the game and after half-time. |
| 2011 | C | Professional Basketball | It helps me a lot; you know playing out there on the court, the ball gets kind of sweaty. It helped me grab the ball better. Yes, it dried my hand up a lot. |

TABLE 1-continued

| Date | Subject | Sport Category | |
|---|---|---|---|
| | | | I was- better than before (re answer to gripping ball better question). It took it a few seconds; when I got on the court, then I got the feel of it, that's when I know it dried it up (re answer to did he feel result of using powder right away). |
| 2011 | D | Professional Basketball | Well actually I fell and got my hands a little wet; so when I used the powder it helped a lot. Actually I went to the free throw line after that and knocked down two free throws. A lot yes (re answer to question dried up hands). Handled A LOT better (re how did he handle the ball after using powder question). Um, probably I was able to grip the ball better with what kind of powder is this? Product? Okay. That's some good powder. So I may check it out. |
| 2011 | E | Professional Basketball | Oh man! Makes the ball feel like its stuck to you; like a yo-yo. Like, I push down, it comes right back up. Dried up real good; made sure I didn't have a lot of sweat on my hands. Great grip (re question did you have a good grip on the ball). All the sweat was gone (re did it dry up immediately question). |
| 2011 | F | Professional Basketball | I can grip the ball better. A lot of times the ball would be slippery and when I put it on, it took a lot of sweat off. It's really good, very nice. I love it. Yes, it really did (re gave better grip on ball question). Before I used, it- it was like the ball was wet; every time I tried to get my hand on the ball, it would slip away from me. But, when I put it on I seem to have a good grip and do what I want to do even better. |
| 2011 | G | College Basketball | It makes the ball easier to grip. Easier to palm the ball; the ball gets wet sometimes from sweat; sometimes you just have a good grip to your hands' and then you can shoot the ball and make better passes. It dries up the sweat; makes your hands less sweaty, and your palms are not sweaty as much during the game. It makes it better to grip the ball. |
| 2011 | H | College Basketball | It was a big effect on my hands. My hands normally sweat, but I used the Product and helped me the whole way. Yes, I was (re helped grip the ball real good question. Everything went great. (12 or 13 free throws.) I enjoyed and I'm going to continue to use it. |
| 2011 | I | College Basketball | Oh golly, the Product was great! It gives you- when you dribble the ball, it helps you a lot. It dried up the sweat up at all. It will give your hands a comfort- it feels like the ball is attached to you when you put it on. No problems after. It goes all through the game. It's probably one of the best powders out. |
| 2011 | J | Professional Basketball | It helped for a period of time, as far as the sweat and everything-but that was about it. Yeah (re answer to question did it dry sweat). To tell you the truth, I could not tell . . . the game, I just put it on and I saw the sweat gone; and I was ready to go. Yeah (re handled the ball really good question). |

A sufficient amount of the formulation can also be used with subjects in need of treatment for skin disorders such as acne as described in table 2.

TABLE 2

| Subject | |
|---|---|
| A | Been to a dermatologist. I have tried 3 different medications; I had an antibiotic, 2 ointments and a skin cleaning pad. Those dried my skin out; I didn't see much improvement; and it was expensive. The product that I am using now has been a great improvement on my skin and it's did a 190 degree turn. And, it's a whole lot smoother, it does not dry my skin out. It keeps it from being oily; and the blemishes have disappeared. Used products 2 weeks. Great improvement in the way my skin has improved. Had dark spots and I broke out real bad with pimples? The dark spots have lighted up and the pimples have decreased. My mother has noticed a big difference in my skin. My skin is a whole lot smoother; it's not as oily as it was. A lot of my co-workers have noticed the difference in my skin; the way it shines and it has a little glow to it now. And, that's my testimony. |
| B | Some comments from 3 Interviews include: I have been using this product for two weeks, and I really like how it feels on my skin. It makes it a lot smoother and less oily. I have had breakouts in the past and they've cleared up; and I just really like how it feels; and I recommend it to anyone that . . . |
| C | Have been using the skin care products for 2 weeks. I seen a dramatic change in my skin on my face; I have had a lot less break outs. My mom has noticed a change in it. A lot of my family members have also noticed that my skin has been sort of like glowing. So, I've been to dermatologists; I've tried Pro-Active; I've tried antibiotics. I've tried everything and this seems to work. I would recommend this to anyone. |
| D | The subject reports: My face skin was messed up so badly that I was not recognized due to an accident. I had badly punctured skin wounds in the face. I still have over 150 holes in my face underneath my skin. My face looked like a dart board and my face had polka dot spots with punctured holes. The doctor told my parent, I need reconstructive surgery. Unfortunately I am from a small town in Mississippi. My mother was a single parent raising five children. We did not have the money for cosmetic surgery. I don't like wearing makeup foundation on my face. I was very ashamed of my face. I wouldn't go anywhere. I was in my first semester of college. I was unable to return to college due to the accident. While in the hospital, my family would not let me look in the mirror. I asked them why later on and they said my face scared them. People were trying to come and see me. I told them don't come to see me, that's what you call depressing. Every doctor that I have seen asked me did I have cosmetic surgery. I tell them I have never had cosmetic surgery on my face. The doctor and nurses go and get other doctors to come look at my x-rays that show all the holes in my face and they can't believe their eyes. Some doctors also made comments like this; I have been in the medical field twenty plus years, never have I seen nothing like this trauma to the face. When I picked up my x-rays, one of the doctor asked me where is the person that had the accident, I replied this is me; she said you must have had a good plastic surgery doctor. I said no and I told her that I have been using a skin care product. This has been a life changing experience for me. Looking at my x-rays, you would never know that I am that person because I still have all those holes underneath my skin; but you can't tell the difference. |

The present in provide a unique novel natural formulation, which can be used in skin care products, cosmetic products, natural organic sport powder, to prevent perspiration in the hands, personal care products such as, deodorant for antiperspirant to keep dry. The formulation replaces talc in many products. The formulation is an alternative for talc, therefore, formulation and talc can be used in the products and have the same effect, however, the formulation are different. However, there is additional advantage and other features of the present invention will be set forth in part in the description that follows and in part will become apparent to those having ordinary skill in the art upon examination of the following or may be learned from the practice of the present invention.

The advantage of the present invention may be realized and obtained as particularly point out in the appended description. The present invention is capable of other and different parts, and its several details are capable of modification in various obvious respects, all without departing from the present invention. The present invention give useful meaning to improving the skin, by preserve the skin in the aging process, less oily skin to help prevent breakouts and blemish, or even making the skin soft and smooth, whereas, the structure and functions of the skin become tighten, more firm, and being able to improve the surface appearance of skin to a natural radiant glow, in particular of facial skin. The cosmetics according to the present advantageously result in a comfortable alternative for talc, which is used in cosmetics products such as, eye-shadow, foundation, blush, and various cosmetics products. As specified above, according to the present invention, the natural organic sport powder may be used for reducing perspiration from the hands, which can give effectively gripping capability, that will enhanced the performance in sports, such as, basketball, football, baseball, tennis, golf, weight lifting, gymnastic, and roping down.

Equivalent elements can be substituted for the ones set forth above such that they perform in substantially the same manner in substantially the same way for achieving substantially the same result. It is believed that the system and method of the present invention and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

The invention claimed is:

1. A seed powder moisture absorbent product made by a process comprising:
   adding a sufficient amount of water to cover a group of long grain seeds to form a first mixture;
   adding a sufficient amount of water to cover a group of whole grain seeds to form a second mixture;
   boiling the first and second mixtures;
   cooling the first mixture to form a thin colorless liquid;
   separating any solid seeds from the colorless liquid of the first mixture;
   cooling the second mixture to form an opaque liquid;
   separating any solid seeds from the opaque liquid of the second mixture;
   combining the thin colorless liquid and the opaque liquid to form a third mixture;
   cooling the third mixture to allow the formation of a film;
   heating the film to form a porous material;
   cooling the porous material to form a residue;
   crushing the residue to form a powder;
   drying the separated solid seeds of the first mixture and the second mixture to form dried seeds;
   crushing the dried seeds to form a dried seed powder;
   combining the dried seed powder with the powder to form the seed powder moisture absorbent product comprised of a long grain seed powder and whole grain seed powder.

2. The product of claim 1 wherein the step of heating occurs in an open pot at between 350-450 degrees F. for about 1 hour.

3. The product of claim 1 wherein the long grain seeds are from a long grain rice plant.

4. The product of claim 1 wherein the whole grain seeds are from a barley plant.

5. The product of claim 1 further comprises the step of blending the product with an ingredient selected from the group consisting of: extract of aloe vera, wheat extract, citric acid, flavoring and natural soy or combinations thereof.

6. The product of claim 1 formulated for use as a deodorant.

7. The product of claim 1 formulated for use as a cosmetic.

8. The product of claim 1 formulated for use as a sports aide.

9. The product of claim 1 formulated for use to treat a skin disorder.

\* \* \* \* \*